US00PP31174P2

(12) United States Plant Patent
Smit

(10) Patent No.: US PP31,174 P2
(45) Date of Patent: Dec. 3, 2019

(54) ***ALOE* PLANT NAMED 'EC-ALOE-1808'**

(50) Latin Name: ***Aloe* hybrid**
Varietal Denomination: EC-ALOE-1808

(71) Applicant: Obed Jacob Smit, Sappemeer (NL)

(72) Inventor: Obed Jacob Smit, Sappemeer (NL)

(73) Assignee: Eden Collection B.V., Sappemeer (NL)

( * ) Notice: Subject to any disclaimer, the term of this patent is extended or adjusted under 35 U.S.C. 154(b) by 0 days.

(21) Appl. No.: 16/350,767

(22) Filed: Jan. 4, 2019

(51) Int. Cl.
*A01H 5/02* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden

(57) ABSTRACT

A new cultivar of *Aloe* plant named 'EC-*ALOE*-1808' that is characterized by dark green leaves with pale yellow dots, leaf margins with non-pointed ridges that are pink-red in color, an erect tulip shaped rosette plant form and a compact habit.

1 Drawing Sheet

Botanical classification: *Aloe* hybrid.
Variety denomination: 'EC-*ALOE*-1808'.

BACKGROUND OF THE INVENTION

The present invention relates to a new and distinct cultivar of *Aloe* plant botanically known as *Aloe* hybrid and hereinafter referred to by the cultivar name 'EC-*ALOE*-1808'.

'EC-*ALOE*-1808' originated from the crossing of the female or seed parent, *Aloe* hybrid 'Carmine' (not patented) with the male or pollen parent, *Aloe* hybrid 'Christmas Carol' (not patented). The crossing was conducted in 2014 in Sappemeer, Netherlands. The resulting seeds were subsequently planted and grown. The cultivar 'EC-*ALOE*-1808' was selected by the inventor in 2016 in a controlled environment as a single plant within the progeny of the stated cross in a cultivated area of Sappemeer, Netherlands.

Asexual reproduction of the new cultivar 'EC-*ALOE*-1808' first occurred by leaf cuttings in 2016 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Aloe* cultivar 'EC-*ALOE*-1808'. These traits in combination distinguish 'EC-*ALOE*-1808' as a new and distinct cultivar apart from other existing varieties of *Aloe* known by the inventor.

1. *Aloe* 'EC-*ALOE*-1808' exhibits dark green leaves with pale yellow dots.
2. *Aloe* 'EC-*ALOE*-1808' exhibits leaf margins with non-pointed ridges that are pink-red in color.
3. *Aloe* 'EC-*ALOE*-1808' exhibits an erect, tulip shaped rosette plant form.
4. *Aloe* 'EC-*ALOE*-1808' exhibits a compact habit.

The closest comparison cultivars are *Aloe* 'Spider' (not patented) and *Aloe* 'Jurassic Dragon' (not patented). 'EC-*ALOE*-1808' is distinguishable from 'Spider' by the following characteristics:

1. *Aloe* 'EC-*ALOE*-1808' exhibits dark green leaves with pale yellow dots. In comparison, the leaves of 'Spider' are pale green with white dots.
2. *Aloe* 'EC-*ALOE*-1808' exhibits leaf margins with non-pointed ridges that are pink-red in color. In comparison, the leaf margins of 'Spider' have short pointed teeth that are pink-white in color.
3. *Aloe* 'EC-*ALOE*-1808' exhibits a compact, erect, tulip shaped rosette plant form. In comparison, the plant form of 'Spider' is not rosette in shape and is less compact.
4. *Aloe* 'EC-*ALOE*-1808' exhibits leaves that are shorter and less-elongated than the leaves of 'Spider'.

'EC-*ALOE*-1808' is distinguishable from 'Jurassic Dragon' by the following characteristics:

1. *Aloe* 'EC-*ALOE*-1808' exhibits leaf margins with non-pointed ridges that are pink-red in color. In comparison, the leaf margins of 'Jurassic Dragon' have pointed teeth that are red in color.
2. *Aloe* 'EC-*ALOE*-1808' exhibits an erect, tulip shaped rosette plant form. In comparison, the plant form of 'Jurassic Dragon' is more open and not as erect.

'EC-*ALOE*-1808' is distinguishable from the female parent plant, by the following characteristics:

1. *Aloe* 'EC-*ALOE*-1808' exhibits dark green leaves with pale yellow dots. In comparison, the leaves of the female parent plant are green with red dots.
2. *Aloe* 'EC-*ALOE*-1808' exhibits a compact habit. In comparison, the female parent plant is even more compact in habit.

'EC-*ALOE*-1808' is distinguishable from the male parent plant by the following characteristics:

1. *Aloe* 'EC-*ALOE*-1808' exhibits dark green leaves with pale yellow dots. In comparison, the leaves of the male parent plant are purple-green with pink-red dots.

2. *Aloe* 'EC-*ALOE*-1808' exhibits leaf margins with non-pointed ridges that are pink-red in color. In comparison, the leaf margins of the male parent plant have pointed teeth that are red in color.
3. *Aloe* 'EC-*ALOE*-1808' exhibits a compact habit. In comparison, the male parent plant is even more compact in habit.

BRIEF DESCRIPTION OF THE DRAWING

The accompanying photograph illustrates the distinguishing traits of *Aloe* 'EC-*ALOE*-1808'. The photograph shows an overall view of a 25 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Aloe* cultivar named 'EC-*ALOE*-1808'. Data was collected in Sappemeer, Netherlands from 25 week old plants grown in a glass greenhouse in 10.5 cm. diameter containers. The time of year was Autumn and the temperature range was 21-24 degrees Centigrade during the day and 18-21 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'EC-*ALOE*-1808' has not been tested under all possible conditions and phenotypic differences may be observed with variations in environmental, climatic, and cultural conditions, however, without any variance in genotype.

Botanical classification: *Aloe* hybrid 'EC-*ALOE*-1808'.
Annual or perennial: Perennial.
Parentage: 'EC-*ALOE*-1808' is a hybrid of the female or seed parent, *Aloe* hybrid 'Carmine' and the male or pollen parent, *Aloe* hybrid 'Christmas Carol'.
Plant type: Potted plant.
Growth habit: Basal rosette of leaves with inflorescences above the leaf plane.
Plant shape: Globe shaped.
Suitable container size: 7.5 cm. pots or larger.
Plant height to top of foliage plane: Average 13.0 cm.
Plant height to top of floral plane: Average 36.1 cm.
Plant width: 16.8 cm.
Vigor: Low to moderate.
Growth rate: Low to moderate.
Low temperature tolerance: 10° Centigrade.
High temperature tolerance: 40° Centigrade.
Propagation: Tissue culture.
Time to initiate roots: Tissue culture plants are placed directly in growing containers.
Crop time: Approximately 25 weeks in Sappemeer, Netherlands.
Root system: Fine and fibrous.
Plant fragrance: None.
Branching habit: Leaves arise in basal rosette, no branches.
Foliage:
*Leaf arrangement*.—Basal rosette.
*Compound or single*.—Single.
*Quantity of leaves per plant*.—Average 12.
*Leaf shape*.—Lanceolate, succulent.
*Leaf aspect*.—Slightly concave.
*Leaf dimensions*.—Average 11.5 cm. in length, 2.8 cm. in width and 0.6 cm. in thickness.
*Leaf apex*.—Long acuminate.
*Leaf base*.—Broad cuneate.
*Leaf texture* (*upper surface*).—Pustulate, narrow oblong ridges, 0.4 cm. in length, 0.1 cm. in width and 0.1 cm. in height.
*Leaf texture* (*lower surface*).—Pustulate, narrow oblong ridges, 0.2 cm. in length, 0.1 cm. in width and 0.1 cm. in height.
*Leaf luster* (*both surfaces*).—Slightly glossy.
*Leaf rugose* (*both surfaces*).—Not rugose.
*Pubescence* (*both surfaces*).—Absent.
*Leaf margin*.—Coarsely dentate-serrate, ridges 0.15 cm. in length, 0.5 cm. in width.
*Venation pattern*.—None visible.
*Young leaf color* (*upper surface*).—NN137C, fading toward base 143A to 143B, oblong ridges 172C margined 147D, leaf margin ridges 171C.
*Young leaf color* (*lower surface*).—136B, fading toward base 137D, oblong ridges 172B margined 147D, leaf margin ridges 171C.
*Mature leaf color* (*upper surface*).—Between 139A and 147A, fading toward base 145D, oblong ridges 172C margined 147D, leaf margin ridges 171C.
*Mature leaf color* (*lower surface*).—Between 147A and N186A, fading toward base 148D, oblong ridges 172B margined 147D, leaf margin ridges 171C.
Flower:
*Inflorescence type*.—Simple raceme.
*Inflorescence dimensions*.—Average 12.4 cm. in height and 4.3 cm. in diameter.
*Quantity of flowers per inflorescence*.—Average 17.
*Quantity of flowers per plant*.—Average 9.
*Quantity of buds per plant*.—Average 8.
*Quantity of flowers and buds per plant*.—Average 17.
*Fragrance*.—None.
*Natural flowering season*.—Fall to winter.
*Time to flower or response time*.—Average 10 months.
*Bud length*.—Average 2.0 cm.
*Bud diameter*.—Average 0.45 cm.
*Bud shape*.—Narrow oblong.
*Bud texture*.—Glabrous.
*Bud luster*.—Matte.
*Bud color*.—35A, tip 147B and 147D.
*Flower type and form*.—Single, tubular.
*Flower aspect*.—Nodding, faded flowers tilt upright before dropping.
*Flower shape*.—Tubular.
*Flower dimensions*.—Average 2.5 cm. in length and 0.85 cm. in diameter.
*Flower longevity*.—Approximately 5 days.
*Persistent or self-cleaning*.—Self-cleaning.
*Tepal arrangement*.—Rotate, tubular, no separate petals or sepals.
*Tepal number*.—Average 6.
*Number of tepal whorls*.—Average 1.
*Tepals fused*.—No.
*Tepal dimensions*.—Average 2.2 cm. in length and 0.5 cm. in width.
*Tepal shape*.—Narrow oblong.
*Tepal tip*.—Acute.
*Tepal base*.—Fused into a tube.

*Tepal margin*.—Entire.
*Tepal margin undulation*.—None.
*Tepal texture* (*both surfaces*).—Smooth.
*Tepal luster* (*both surfaces*).—Matte.
*Tepal rugosity* (*both surfaces*).—Not rugose.
*Tepal color, when opening* (*upper surface*).—35B, fading toward tip 36C, toward end of tip 147B.
*Tepal color, when opening* (*lower surface*).—35A, fading toward tip 36C, toward end of tip 147A and 147B.
*Tepal color, fully opened* (*upper surface*).—35B, fading toward tip 36C, toward end of tip 147B.
*Tepal color, fully opened* (*lower surface*).—35A, fading toward tip 36C, toward end of tip 147A and 147B.
*Tepal veins*.—Absent.
*Tepal color, when fading* (*both surfaces*).—31A, fading toward tip 36C, toward end of tip 148A.

Calyx:
*Calyx shape*.—Tubular.
*Calyx dimensions*.—Average 2.2 cm. in length and 0.85 cm. in diameter.

Peduncle:
*Peduncle dimensions*.—Average 35.3 cm. in length and 0.2 cm. in diameter.
*Peduncle angle*.—Average 5 degrees from vertical.
*Peduncle strength*.—Moderate.
*Peduncle texture*.—Smooth, covered with thin waxy layer.
*Peduncle luster*.—Matte.
*Peduncle color*.—Between 197A and N199A, waxy layer 198A.

Pedicel:
*Pedicel dimensions*.—Average 0.7 cm. in length and 0.075 cm. in diameter.
*Pedicel angle*.—Average 45 degrees from peduncle axis.
*Pedicel strength*.—Moderately strong.
*Pedicel texture*.—Smooth.
*Pedicel luster*.—Matte.
*Pedicel color*.—178B.

Bracts: A single bract is located below each pedicel.
*Bract shape*.—Narrow obovate.
*Bract dimensions*.—0.4 cm. in length and 0.2 cm. in width.
*Bract margin*.—Entire.
*Bract tip*.—Acute.
*Bract base*.—Cuneate.
*Bract color*.—156D.

Reproductive organs:
*Stamen number*.—Average 6 per flower.
*Filament length*.—Average 2.2 cm.
*Filament color*.—14D, toward base 31D.
*Anther shape*.—Narrow oblong, dorsifixed.
*Anther length*.—Average 0.2 cm.
*Anther width*.—Average 0.05 cm.
*Anther color*.—N25B.
*Amount of pollen*.—Abundant.
*Pollen color*.—35A.
*Number of pistils*.—1.
*Pistil length*.—Average 2.1 cm.
*Stigma shape*.—Pointed.
*Stigma dimensions*.—Average 0.2 cm. in length and 0.075 cm. in diameter.
*Stigma color*.—11B.
*Style length*.—Average 1.9 cm.
*Style color*.—153D.
*Ovary color*.—153B.

Fruit and seed: 'EC-*ALOE*-1808' has not produced fruit or seed to date.

Disease and pest resistance: Disease and pest resistance has not been observed.

The invention claimed is:

1. A new and distinct variety of *Aloe* plant named 'EC-*ALOE*-1808' as described and illustrated.

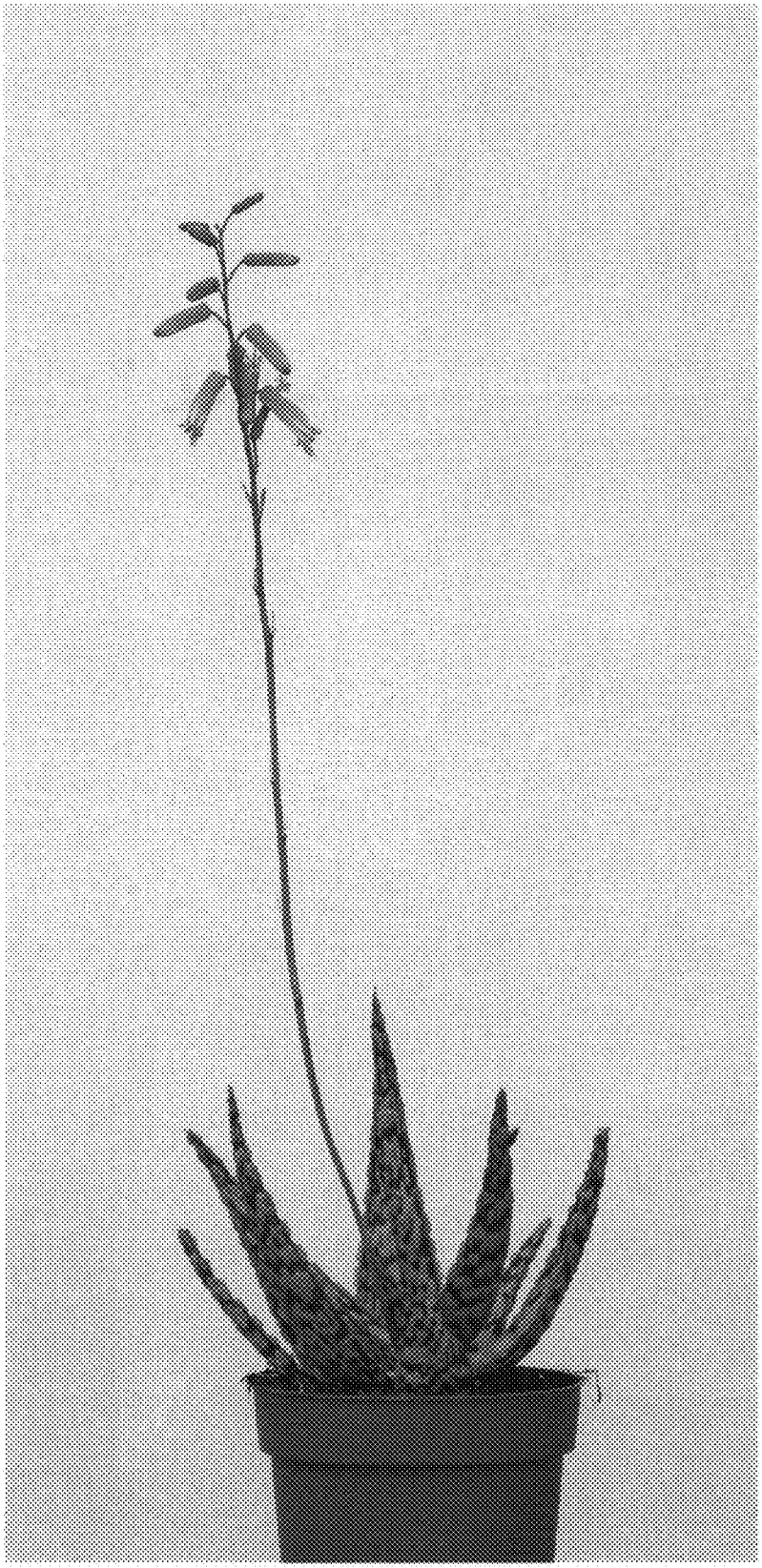

* * * * *